United States Patent [19]

Kifune

[11] 4,445,885

[45] May 1, 1984

[54] INSULIN RELEASING SUPPLIER

[75] Inventor: Koji Kifune, Nara, Japan

[73] Assignee: Unitika, Ltd., Magasaki, Japan

[21] Appl. No.: 78,630

[22] Filed: Sep. 25, 1979

Related U.S. Application Data

[63] Continuation of Ser. No. 877,782, Feb. 14, 1978, abandoned.

[30] Foreign Application Priority Data

Feb. 16, 1977 [JP] Japan ................................. 52-17543
Feb. 24, 1977 [JP] Japan ................................. 52-20024
Feb. 24, 1977 [JP] Japan ................................. 52-20025
Mar. 23, 1977 [JP] Japan ................................. 52-32587

[51] Int. Cl.³ ........................ A61M 1/03; B01D 13/00
[52] U.S. Cl. .................................... 604/28; 210/645;
210/500.2; 210/927; 604/50; 604/66
[58] Field of Search ............ 210/22 R, 500 M, 321 B,
210/645, 927, 500.2; 128/213 R; 424/178;
604/28, 50, 66

[56] References Cited

U.S. PATENT DOCUMENTS 2,076,082  4/1937  Hagedorn et al. ................... 424/178
3,827,565  8/1974  Matsumura ........................... 210/22
4,056,467  11/1977  Christen et al. ............ 210/500 M X
4,077,407  3/1978  Theeuwes et al. ............. 128/213 X Primary Examiner—Frank A. Spear, Jr.
Attorney, Agent, or Firm—Sughrue, Mion, Zinn, Macpeak, and Seas

[57] ABSTRACT

An insulin supplier, which can be effectively used for the treatment of diabetic patients, comprising a casing and at least one tubular structure composed of a polymeric semipermeable membrane to provide an internal chamber inside of the tubular membrane and an external chamber outside of the tubular membrane, either one of the internal chamber and the external chamber having at least one fluid-inlet and at least one fluid-outlet; wherein blood or another body fluid is introduced into that chamber which has the at least one fluid-inlet and the at least one fluid-outlet and a solution of insulin is introduced into the other chamber, whereby insulin in an effective amount required for metabolism within the body is supplied to the blood or the body fluid depending on the blood glucose level through the polymeric semipermeable membrane between the internal and external chambers over a long period of time.

10 Claims, 4 Drawing Figures

INSULIN RELEASING SUPPLIER

This is a continuation of application Ser. No. 877,782, filed Feb. 14, 1978, now abandoned.

BACKGROUND OF THE INVENTION

1. Field of the Invention

This invention relates to a device for controlling blood sugar levels in man, and specifically, to a device for treating diabetic patients.

2. Description of the Prior Art

Diabetes denotes a metabolic disorder caused by a loss in the function of $\beta$-cells of the islands of Langerhans in the pancreas of man, which results in their inability to perform a normal secretion of insulin and thus in an insufficient metabolism of blood glucose caused by insulin which eventually leads to an abnormally increased glucose level in the blood. The blood glucose levels of diabetic patients increase at most to about 500 mg%, whereas normal healthy persons have an average blood glucose level of about 80 to 100 mg%.

The one-shot insulin therapy of repeated injections of insulin at intervals of 1 to several days has heretofore been employed to reduce high glucose levels in the blood to normal glucose levels. This method has an effect of reducing the blood glucose level for a certain period of time, but is not sufficient for maintaining the blood glucose level always at an appropriate value. Accordingly, fluctuations in glucose level by external causes such as meals cannot be prevented, and there have been many cases in which diabetic patients suffer from, and die of, renal or cerebral disorders caused by fluctuations in blood glucose levels. An ideal method for treating serious cases of diabetes is to supply insulin depending on the glucose level within the body. In order words, it is desirable to supply insulin in an amount corresponding to the increase in the blood glocuse level, and to stop the insulin supply when the blood glucose level has returned to a normal level.

Methods under investigation in an attempt to establish such an ideal method include a method which is based on linking a glucose sensor to an insulin injector. This method is described, for example, in "Computer Stimulation of the Glucose Regulatory System in Man", *Diabetes* 19; 1373, (1970). The method involves injecting a required amount of an insulin solution from an injection syringe into the body depending on the glucose level detected by the glucose sensor thereby to maintain the blood glucose level at a normal value. According to this method, however, many accessory devices such as a computer for connecting the injection syringe to the glucose sensor are necessary, and the device as a whole has a large-size. Many problems still have to be solved to put such a device into actual practice.

According to another known method, $\beta$-cells removed from the pancreas are cultivated, and are used to perform their inherent function of detecting the blood glucose level in the blood which is present on the other side of a macroporous wall (not a semipermeable membrane) and then releasing insulin, thereby to supply insulin to the blood. Such a method is described, for example, in "A Hybrid Artificial Pancreates" *Trans. Amer. Soc. Artif. Int. Organs.*, 21 8–15 (1975). However, since the tissue culture of the $\beta$-cells is difficult, and the cultivated $\beta$-cells have a short life, this method is far from practical.

SUMMARY OF THE INVENTION

In view of the state of the art, extensive investigations have been made in an attempt to develop a small, simple and practical device which can be used to supply insulin in a manner as close to the insulin secretion of the pancreas as possible. As a result, it has been found that when an aqueous solution of insulin and the blood are caused to be present with a tubular polymeric semipermeable membrane placed therebetween, insulin together with water passes continuously at a constant rate and with a very good efficiency into the blood through the polymeric semipermeable membrane; the rate of movement varies depending on the fluctuation of the glucose concentration in the blood; the rate of movement can be controlled with a high precision by flowing the aqueous solution of insulin; and that using such a method, the amount of insulin required for metabolism in the human body can be transferred, and this can be utilized effectively for the treatment of diabetic patients. This discovery has led to the accomplishment of the present invention.

The present invention provides an insulin supply means or insulin supplier comprising a casing and at least one tubular structure composed of a polymeric semipermeable membrane to provide an internal chamber defined by the space inside the tubular polymeric semipermeable membrane and an external chamber outside the tubular polymeric semipermeable membrane defined by the space between the casing and the tubular polymeric semipermeable membrane, either one of the internal chamber and the external chamber having at least one fluid-inlet and at least one fluid-outlet; wherein the blood or another body fluid is introduced into that chamber which has the at least one fluid-inlet and the at least one fluid-outlet such that when a solution of insulin is introduced into the other chamber, insulin in the amount required for metabolism within the body is supplied to the blood or the body fluid depending on the blood glucose level through the polymeric semipermeable membrane between the internal and external chambers over a long period of time.

BRIEF DESCRIPTION OF THE ACCOMPANYING DRAWINGS

FIG. 2 (B) is a model view showing the inlets and outlets provided on the surface of a casing.

DETAILED DESCRIPTION OF THE INVENTION

Figure 1:
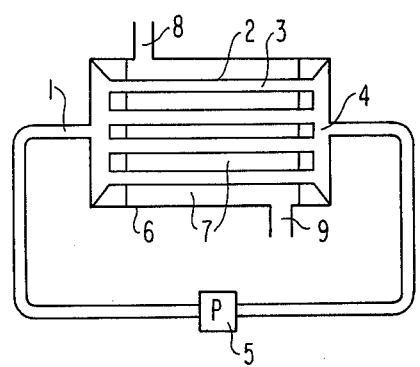
FIG. 1 is a cross-sectional view of a model showing one example of the insulin supplier of this invention in which the blood is introduced into an external chamber of hollow fibers, and a solution of insulin is pumped through the inside of the hollow fibers.

The insulin supplier in accordance with this invention is a simple device comprising a casing and a tubular structure of a polymeric semipermeable membrane, and can have a small size. The insulin supplier has superior performance and can be used over an extended period of time. Accordingly, diabetic patients who utilized the insulin supplier of this invention can perform daily activities with the insulin supplier mounted in or on their body.

The insulin supplier of this invention comprises essentially a casing, at least one tubular structure composed of a polymeric semipermeable membrane, at least one fluid-inlet and at least one fluid-outlet. The tubular structure is present in the casing to provide an internal chamber which is formed by the space inside the tubular polymeric semipermeable membrane and an external chamber which is formed outside of the tubular polymeric semipermeable membrane by the space between the tubular polymeric semipermeable membrane and the casing. The fluid-inlet and the fluid-outlet are provided in either the internal chamber or the external chamber. The blood is introduced into that chamber having the fluid-inlet and outlet, and a solution of insulin is introduced into the other chamber. At this time, the metabolically required amount of insulin is supplied to the blood through the polymeric semipermeable membrane between the internal and external chambers.

In the above structure an insulin supplier in which the fluid-inlet and the fluid-outlet are provided in both of the internal and external chambers and the fluid-inlet and fluid-outlet of that chamber with the insulin solution are linked to a device capable of flowing the insulin solution is especially preferred because the insulin solution is moved while it is being used, and insulin can be supplied to the blood with a high precision and over an extended period of time.

The term "polymeric semipermeable membrane", as used in the description of the present invention, denotes a polymeric membrane which has pores of sizes that permit the passage of insulin (the highest molecular weight of insulin generally used as a therapeutic agent is about 20,000 which is the molecular weight of insulin trimer), and does not permit the passage of polymeric substances or solids having larger sizes.

In the present invention, the polymeric semipermeable membrane is used in the form of a tubular structure. The cross-sectional shape of the tubular structure is not limited, and may, for example, be triangular, polygonal, circular or elliptical. In the present invention, a polymeric semipermeable membrane in the form of hollow fibers is especially preferably used. Hollow fibers are desirable because the flow pressure of a liquid flowing through the inside of the hollow fibers can be maintained at high levels, and a sufficient membrane surface area can be achieved in the smallest possible space. Especially suitable hollow fibers which can be used have the following dimensions.

Inside diameter: about 50 to 400$\mu$, preferably 100 to 250$\mu$.
Thickness: about 10 to 50$\mu$, preferably 15 to 30$\mu$.
Pore size: about 100 Å to 2$\mu$, preferably 0.1 to 1$\mu$.

In actual use, the sizes of the hollow fibers are desirably chosen from the above ranges depending on the amount of insulin required by the blood and the speed of passage of insulin which must be supplied. Hollow fibers having sizes outside the above ranges can also be used for the purpose of the present invention. However, if such a semipermeable membrane is used, it is very likely that the function of the polymeric semipermeable membrane as a glocuse sensor, which is one of the characteristics of the present invention, will become insufficient.

Examples of polymers which can be used to form the semipermeable membrane employed in this invention are natural polymers or derivatives of natural polymers such as cuprophane, cellulose acetate, regenerated cellulose and collagen and synthetic polymers such as polyvinyl alcohol, polyion complexes (e.g. sodium polystyrene sulfonate, polyvinylpyrrolidone chloride, etc.), polyvinyl pyrrolidone, hydrogels (e.g., polyhydroxyethyl methacrylate, etc.), polyamides (e.g., polyhexamethylene-adipamide, N-alkoxyalkyl polyhexamethylene-adipamide, etc.), polyesters (e.g., polyethylene terephthalate, etc.), polyacrylonitrile and polysiloxanes (e.g., polydimethyl siloxane, etc.). While the molecular weight of the polymer used for producing the polymeric semipermeable membrane used in this invention will differ dependent on the type of polymer used, generally, a suitable molecular weight is more than about 7,000 and preferably, more than 10,000.

The method for preparing hollow fibers from these polymers described above will vary depending on the type of polymer, and methods, e.g., known in the art, appropriate to the individual polymers can be employed. For example, the production of hollow fibers using cuprophane is disclosed in Japanese Patent Application (OPI) No. 59518/75 and the production of hollow fibers using polyacrylonitrile is disclosed in U.S. Pat. No. 3,851,036. U.S. Pat. No. 3,494,780 discloses a process for enhancing the permeability of cellulose acetate separatory membranes, U.S. Pat. No. 3,940,469 discloses a process for forming semipermeable hollow fibers using a polyamide, and a process for producing cellulose type-hollow fibers is disclosed in British Pat. No. 514,638. The method for producing the pores therein is thus important. More specifically, in the case of cuprophane, regenerated cellulose and polyvinyl alcohol, voids occur by properly choosing the composition of the coagulation bath used and the temperature conditions employed at the time of wet spinning. These voids become pores during filament formation. In the case of cellulose acetate, desirable pores can be formed by properly choosing the composition of the solvent used at the time of dry spinning. In the case of polyamides and polyesters, a water-soluble or solvent-soluble substance such as polyethylene oxide is added at the time of melt spinning, and after filament formation, this substance is removed from the filaments to form pores.

In the present invention, at least one tubular structure of a polymeric semipermeable membrane is used. In order to secure a large membrane surface area, it is desirable to use as many tubular structures as possible. If, however, too many tubular structures are used, the size of the overall insulin supplier becomes undesirably large.

When hollow fibers are used as the polymeric semipermeable membrane in the present invention, the number of hollow fibers used per insulin supplier is about 30 to 500, preferably 50 to 200. By using this number of hollow filaments, the size of the insulin supplier of this invention can be decreased, and for example, the length of the insulin supplier can be as small as about 1 to 10 cm. Thus, an insulin supplier having an inner capacity (i.e., the capacity inside the casing) of as small as about 20 cm$^3$ can be fabricated. Even when the amount of the blood to be treated is very small, the purpose of the present invention can be fully achieved. Hence the insulin supplier of the present invention is advantageous in actual use.

To hold the tubular structure within the casing to separate the inside of the casing into an internal chamber and an external chamber, an adhesive resin, for example a curable resin such as a silicone resin (e.g., a polydimethyl siloxane, etc.), a polyurethane resin (e.g., a polypropylene oxide phenyl urethane urea, etc.) or an epoxy resin (e.g., an epoxy-polyamine type resin, etc.) can be used. Parallel-arranged tubular structures can be held in place, for example, by dipping them in a solution of an uncrosslinked resin of the above-exemplified type, and after allowing the resin to crosslink, cutting the resin perpendicularly to the axial direction of the parallel arranged tubular structures thereby to expose the inner pores. At this time, the outside of the resin containing the tubular structures adheres firmly to the casing.

The term "insulin", as used herein in the description of the present invention, denotes insulin and derivatives thereof. Examples of these forms of insulin are regular insulin, semi-lente insulin, isophane insulin, lente insulin, protamine zinc insulin, and ultra insulin. The insulin as used in this invention can be employed in the form of an aqueous solution or an emulsion. Generally, insulin has low solubility in water at 25° C. and therefore, insulin preferably is used at a pH of about 2.5 to 3.5 at which the solubility of insulin is good. The saturated concentration of insulin in water under these conditions is about 30 mg%, and if insulin is added in a larger amount, the excess is present as a solid phase in the aqueous solution. However, since fresh insulin dissolves as the insulin is consumed, a solution of insulin having an insulin solid phase can also be used in this invention. Rather, for use over a long period of time, the presence of an insulin solid phase is advantageous. In any case, since the concentration of solute in an insulin solution even under saturation conditions is much more dilute than the solute concentration of the blood, no problem is posed in using the insulin supplier of this invention.

The blood, as referred to in the description of the present invention, denotes not only blood flowing through vascular vessels within the body, but also body fluids present in all parts of the human body such as a body fluid in the abdominal cavity or a lymphatic fluid in the subcutaneous muscles.

Turning now to the Figures, FIG. 1 is a cross-sectional view of a model of one example of the insulin supplier of this invention. An insulin solution which flows into the insulin supplier from an inlet 1 passes through an internal chamber 3 within hollow fibers 2 and flows out from an outlet 4, and is circulated to a pump 5. On the other hand, the blood flows into the insulin supplier from an inlet 8, passes through an external chamber 7 outside of the hollow fibers, and flows out from an outlet 9.

Figure 2A:
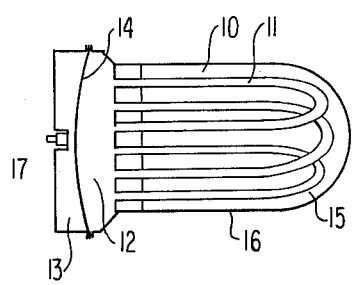
FIG. 2 (A) is a cross-sectional view of a model showing another example of the insulin supplier of this invention in which the blood is introduced into an external chamber having a plurality of inlets and outlets and a solution of insulin inside of the hollow fibers always pressurized by a gas chamber provided in contact with a reservoir for the insulin solution.
Figure 2B:
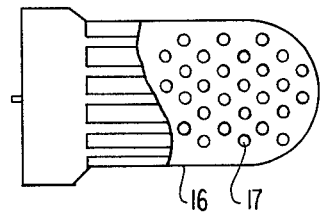

FIGS. 2 (A) and 2 (B) show a cross-sectional view of a model showing another example of the insulin supplier of this invention which has a plurality of inlets and outlets in the chamber into which the blood flows. A solution of insulin is filled in an internal chamber of hollow fibers 10, and is pressurized by a diaphragm valve 14 provided in contact with a reservoir 12 for the insulin solution. The diaphragm valve 14 has a gas pressure chamber 13, and a required amount of an inert gas, e.g., nitrogen, argon, etc., is injected from an injecting valve 17.

The method for introducing the blood to the supplier differs depending on the site at which the insulin supplier of the invention is to be located. As shown in FIG. 1, two pipes for introducing and discharging the blood are provided in the external chamber, and a vascular vessel is connected to both ends of the pipes to circulate and introduce the blood. Alternatively, as shown in FIG. 2 (B), a number of small holes 17 which connect the external chamber and the outside environment are provided on the outer wall of casing 16 of the external chamber to permit contact of the surfaces of the hollow fibers with the blood. Since an insulin supplier of the type shown in FIG. 2 can be produced in a very compact size, this type can be used implanted in a very narrow space of the body such as in a body cavity and therefore, is especially advantageous.

FIG. 2 shows a type of insulin supplier in which an insulin solution is pressurized indirectly through a diaphragm valve. A method of pressurizing an insulin solution by providing a gas-injecting space without a diaphragm valve and introducing a gas under pressure into this space can also be applied to the insulin supplier of this invention.

In FIG. 1, an insulin solution is circulated into the internal chamber within the hollow fibers, and the blood is introduced into the external chamber outside of the hollow fibers. Conversely, it is possible to introduce the blood into the internal chamber within the hollow fibers, and introduce the insulin solution into the external chamber located outside of the hollow fibers.

In either case, insulin can pass into the blood due to the difference of osmotic pressure. When the insulin solution is to be passed in the insulin supplier of this invention, it is very advantageous to pass the insulin solution through the internal chamber within the hollow fibers, because this makes a precise control of the amount of insulin passed over a wider range possible.

A liquid conveying pump is an example of a means capable of passing a fluid in the insulin supplier of this invention. Specific types are, for example, micrometering pumps in general use, such as a pipe shearing type pump or a piston type pump. The amount of flow of the insulin solution generated by such a pump is determined by the amount of insulin required by the blood and with an ordinary tubular structure the desirable flow rate of insulin is 0.1 ml/min. to 10 ml/min., preferably 0.5 to 2 ml/min.

The amount of insulin generally required by diabetic patients is about 80 m USP insulin unit/min. (1 USP insulin unit being the amount of insulin required to cause the metabolism of 1.5 g of glucose) when the glucose level is 300 mg%, and the insulin supplier is designed using this amount as a standard.

When an insulin solution and the blood are present with a semipermeable membrane therebetween in the insulin supplier of this invention, the theory of the passage of the insulin to the blood is described below:

When an insulin solution is transported through a narrow circular tubular flow passage, the pressure $P_I$ at a given point in the internal chamber of the inside of the hollow fibers is given by the following equation:

$$P_I = P_E + \Delta P = P_E + K \cdot \frac{\bar{\mu} l}{D^2}$$

wherein $P_E$ is the pressure (in g/cm$^2$) at the inlet of the tube;

ΔP is the pressure difference between the inlet of the tube and a point at a length l (in cm) from the inlet of the tube;

K is constant number;

D is the inside diameter (in cm) of the tube; and $\bar{u}$ is the average flow rate (in cm/sec) through the tube.

If the pressure (in g/cm$^2$) in the blood flowing outside the semipermeable membrane at the same point as the insulin solution is $P_B$, the simple pressure $P_T$ (in g/cm$^2$) of the membrane which presses on the blood from the side of the insulin solution is given by $P_T = P_I - P_B$. If the inside diameter of the tubular structure of the membrane is small, the relation $P_I > P_B$ always holds good even if the flow rate of the blood changes somewhat. Hence, $P_T > 0$. In addition to the above, the osmotic pressure present between the blood and the insulin solution through the polymeric semipermeable membrane should be considered as a component of the pressure. Since the blood has solute at a much higher concentration in comparison with the insulin solution, an osmotic pressure is exerted from the insulin solution onto the blood. The osmotic pressure (in g/cm$^2$) is given by the equation $P_o = nRT/V$ wherein V is the volume (in cm$^3$), n is the moles of the total solute dissolved, R is the gas constant, and T is the absolute temperature (in °K.). Accordingly, the pressure acting to push on the semipermeable membrane from the insulin solution toward the blood, namely the true force to release the solution present in the internal chamber (especially to release water to the blood) is given by $(P_T + P_o)$. Since the $(P_T + P_o)$ value is a function of the concentration of the glucose present in the blood, the amount of insulin passed increases as the glucose concentration increases, and decreases as the glucose concentration decreases. Thus, when the amount of glucose increases, insulin is released together with the passing water. When the amount of glucose is small, the extent of release is low. This shows that the polymeric semipermeable membrane acts as a glucose sensor. Accordingly, by selecting an optimum material for the semipermeable membrane, an optimum pore size, an optimum size of the flow path, and designing the supplier such that the $(P_T + P_o)$ value is low when the blood glucose level is about 100 mg% which is a normal level, and that this pressure is affected by the osmotic pressure as the glucose level increases, a metabolically required amount of insulin can be released depending on the variation in the blood glucose level. In this manner, the polymeric semipermeable membrane in the present invention acts like the beta cells within the living body.

When the blood is passed through the internal chamber within the hollow fibers, the movement of the insulin solution depends only on the osmotic pressure, and the flowing pressure becomes substantially negative.

The surface of the insulin supplier which comes into contact with the blood, except for the tubular polymeric semipermeable membrane, should desirably be made of a material which has a good affinity for the living body, namely a material which does not cause a coagulation of the blood. Examples of such materials are cellulose resins, polysiloxanes, polyion complexes, polyurethanes and hydrogels. Where materials having a relatively poor biological affinity such as glass, polyethylene, epoxy resins, polyamides, polyacrylonitrile, and polyesters are used, the surfaces thereof should preferably be coated or treated with the above-exemplified resins, or treated with an anticoagulant such as heparin, urokinase or citric acid to form a new surface. For example, in the treating, the surface is roughened, glutaraldehyde is adhesively coated on the roughened surface and then an anticoagulant is coated thereon. Suitable methods of accomplishing this are described in U.S. Pat. Nos. 3,453,194, 3,511,684 and 3,625,745.

Also at those tubular polymeric semipermeable membranes which have a poor biological affinity such as polyamides and polyesters their surface, especially the portion contacting the blood should preferably be treated with an anticoagulant.

If the amount of the insulin solution which is flowed is changed depending on the change in the amount of glucose in the blood, a more precise and more subtle control of the blood glucose level can be performed by the insulin supplier of this invention. Such a control is possible by sensing abnormal values incident to a change in the blood glucose level, such as changes in the blood glucose level, blood pH (the blood of normal persons usually has a pH of 7.4, and that of seriously diabetic patients has a pH of 6.9), and the cholesterol level, and sending the sensed values to, for example, an electrical motor for a pump. For example, when the amount sensed becomes large, a large electrical current flows in the motor to increase the amount of flow, and when the amount sensed is small, the amount of electric current flow can be reduced.

An example of the means of sensing such abnormal changes in a glucose oxidase electrode, e.g., described in Samuel P. Bessman, *Trans. Amer. Soc. Artif. Intern. Organs,* 1973, 19. 361–369. When glucose oxidase acts on glucose, gluconic acid and $H_2O_2$ form (according to equation (1) below). When a platinum-silver electrode is set up in this reaction system, $H_2O_2$ is oxidized by the platinum to release two electrons (according to equation (2) below). The oxidized $H_2O_2$ is reduced by the silver to $H_2O$ (according to equation (3) below). In this reaction system, a potential difference is generated between the platinum electrode (anode) and the silver electrode. This potential difference increases as the concentration of the glucose in the blood increases. A glucose sensor is based on the utilization of this principle.

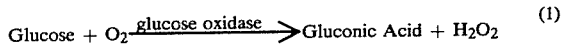

(1)

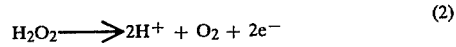

(2)

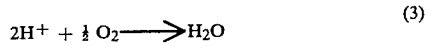

(3)

And over all

In applying this principle to the present invention, it is most appropriate to fabricate the sensor itself in a small size because it is used continuously in the flow of the blood, and to use an enzyme immobilized electrode consisting of glucose oxidase fixed to a carrier so that long-term use is possible. The electrode portion is to be implanted in the blood, but for the simplification of the process, the electrode portion can also be placed in the external chamber as shown in FIG. 2. Since the potential difference generated between these electrodes is usually not more than 1 mV, an amplifier should be provided between a potentiometer and a driving section in order to increase this potential difference as a signal for a driving motor.

The insulin supplier of the present invention can be implanted in the human body at an endocorporeal blood-flowing portion or in an endocorporeal space in which a body fluid is present, such as the abdominal cavity, or a subcutaneous muscular portion containing capillary vessels and lymphatic glands. When a pump is provided to flow the insulin solution through the insulin supplier, the insulin supplier of the invention is effectively provided in the path of blood. Also an insulin supplier of the pressuring type is especially effective when it is implanted inside the body, such as at a portion where a body fluid is present.

Figure 3:
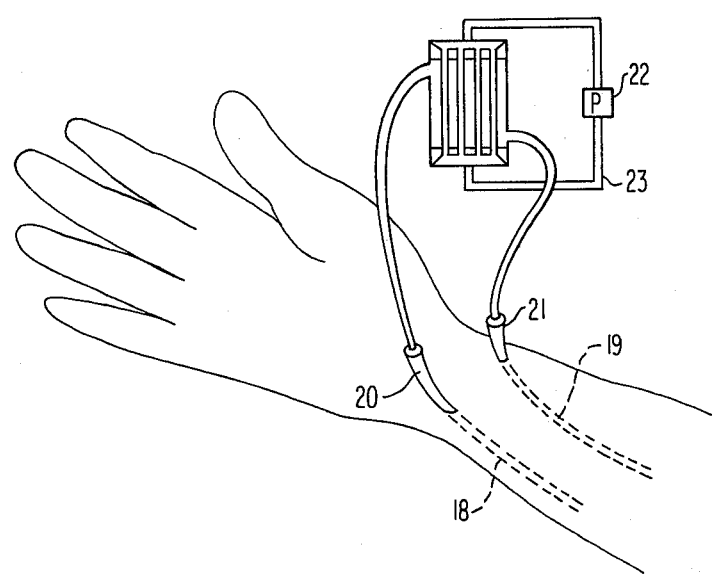
FIG. 3 is a schematic view showing the method of mounting the insulin supplier shown in FIG. 1 between an arterial radialis and a venous radialis of the forearm of the human body.

One example of setting up the insulin supplier of this invention in the flow path of the blood is shown in FIG. 3. FIG. 3 shows the forearm and hand of a human body in which 18 represents an arterial radialis and 19 represents a venous radialis.

The insulin supplier of this invention can be provided between 18 and 19. Through canula 20 and 21 connected to the blood vessels, the blood flowing out from the artery 18 is recycled to the vein 19 through the supplier as a by-pass. The insulin supplier shown in FIG. 3 utilizes hollow fibers, and a solution of insulin within the hollow fibers is circulated at a given flow rate through a pipe 23 from a pump 22.

The following Examples are given to further illustrate the present invention more specifically.

EXAMPLE 1

This Example is an in vitro Example.

The example was performed using an insulin supplier of the type shown in FIG. 1. The tubular structure comprised 120 hollow fibers (inside diameter: 210$\mu$; thickness: 25$\mu$) of cellulose acetate produced by dry spinning using a water-acetone mixture (water content: 15% by volume) as a solvent. The length of that portion of the tubular structure which contacted the blood was adjusted to 3 cm. Both ends of the hollow fibers were bundled and held by an epoxy resin (an equal weight mixture of Araldite AW 106 and HV 953u produced by Ciba-Geigy). A casing which enclosed an external chamber through which the blood passed was a circular cylinder having an inside diameter of 1 cm. The inner wall of the cylinder was coated with a polyurethane (a polyurethane urea segment in which the polypropylene oxide has a molecular weight of 1210) to prevent a coagulation of the blood.

An aqueous solution of regular insulin in a concentration of 50 mg% which has a pH of 3.0 was introduced into the internal chamber within the hollow fibers. A silicone rubber pipe with an inside diameter of 3 mm was used to connect the internal chamber to a liquid conveying pump to circulate the insulin solution.

For this example fresh blood from a healthy person within 8 hr. after collection was used after addition of 2 wt% sodium citrate. That blood was passed at a rate of 100 ml/min. through blood inlet 8 and was discharged from blood outlet 9 after maintaining the blood in complete contact with the surface of the hollow fiber membrane.

Separately, the same human blood was mixed with glucose of varying concentrations. Each of the mixtures was passed through the insulin supplier in the same way as described above. Table 1 summarizes the amount of insulin released into the blood containing glucose in varying concentrations. The insulin was followed using a tracer of insulin labelled with $^{125}I$ mixed with non-labelled insulin, and the $\gamma$-ray level in the blood was measured using a scintillation counter.

TABLE 1

| Run No. | Flow Rate of Insulin Solution (ml/min.) | Glucose Concentration (mg %) | Amount of Insulin Released (mUSP unit/min.) |
|---|---|---|---|
| 1* | 1.0 | 98.5 | 14.2 |
| 2 | " | 189.0 | 31.2 |
| 3 | " | 272.5 | 62.9 |
| 4 | " | 391.5 | 96.5 |
| 5 | " | 269.0 | 57.2 |
| 6 | " | 179.5 | 32.1 |
| 7* | " | 101.0 | 3.8 |
| 8* | 2.0 | 95.0 | 18.3 |
| 9 | " | 196.5 | 45.9 |
| 10 | " | 301.0 | 84.1 |
| 11 | " | 435.5 | 129.3 |
| 12 | " | 329.5 | 84.6 |
| 13 | " | 209.0 | 53.6 |
| 14* | " | 99.5 | 8.8 |

*Human blood without addition of glucose

Run Nos. 1 to 7 and Run Nos. 8 to 14 each were one block. The example was performed in the order of Run Nos. 1 to 7, and Run Nos. 8 to 14. At the beginning of each Run, the insulin supplier was washed with human blood containing no glucose.

The glucose concentration was measured using Glucose Analyzer Model 23A (produced by the Yellow Springs Instrument Co.)

In this Example, the blood flow rate of 100 ml/min was prescribed on the assumption that the insulin supplier of this invention was set up between an arterial radialis and a venous radialis as shown in FIG. 3.

Table 1 shows the amount of insulin released when glucose was added to the blood of a normal healthy person and the amount of glucose was increased to about 400 mg% which is the blood glucose level of an advanced diabetic patient, and then decreased artificially until the blood glucose level of a normal healthy person was reached. The results shown in Table 1 show that even though the other conditions, except the glucose concentrations, were the same, the amount of insulin released increases with increasing concentration of glucose, and the increase of insulin is substantially proportional to the increase in the glucose concentration. It is noted that insulin was released in an amount of 60 to 90 mUSP insulin unit/min. when the glucose concentration was near 300 mg%, and this amount of insulin substantially coincided with the amount of insulin (80 mUSP insulin unit/min.) required for metabolism by a diabetic patient. When the glucose concentration was near 100 mg% which is the blood glucose level of a normal healthy person, the amount of insulin released was small. Thus, in the insulin supplier of this invention, the polymeric semipermeable membrane functioned as a sensor, and could easily be designated as artificial $\beta$-cells. Furthermore, the relative values of the amount of insulin released could be somewhat increased by increasing the flow rate of insulin from 1.0 ml/min. to 2.0 ml/min. This suggests the same insulin supplier could easily be used for patients who required different amounts of insulin. Accordingly, it ca be readily inferred from this that when the insulin supplier of this invention is used attached to the human body in the manner shown in FIG. 3, a suitable amount of insulin is released from the insulin supplier depending on the amount of glucose in the flowing blood, and the blood glucose level can be maintained always in a stable condition.

EXAMPLE 2

This Example also is an in vitro example.

The insulin supplier used was of the type shown in FIG. 2. An insulin solution having a concentration of 100 mg% (a part of the insulin was present as an insulin solid phase) was placed in a reservoir 12 leading to the inside of the hollow fibers. The hollow fibers were prepared from nylon 6 by melt spinning nylon 6 together with 10% by weight of polyethylene oxide with a molecular weight of about 8000, and extracting the resulting fibers with hot water at 95° C. to remove the polyethylene oxide. The number of hollow fibers was eighty five and each of them had an inside diameter of 150μ, a wall thickness of 18μ and an effective fiber length of 8 cm. Nitrogen gas was introduced from a pressure bomb into a gas chamber located outside the reservoir and containing a diaphragm therein, and the pressure of the inside of the reservoir was maintained at 120 mm H$_2$O. A number of small holes with a diameter of 3 mm were provided on the casing. The internal chamber had a capacity of 10 cc; the insulin solution reservoir, 5 cc; and the gas chamber, 5 cc.

The insulin supplier was dipped in 100 ml of the bovine serum (obtained by centrifuging fresh bovine blood at a speed of 5000 rpm), and the serum was agitated. Insulin (1 μCi) labelled with $^{125}$I has been added to the insulin solution within the inside of the hollow fibers. After the dipping of the insulin supplier in the serum, the γ-ray level in the serum was measured from time to time, and the amount of insulin released from the insulin supplier was calculated. As another run, 300 mg% of glucose was added to the same serum, and the mixture was subjected to the same procedures as described above. Variations with time of the amount of insulin released are shown in Table 2 below.

TABLE 2

| Time Elapsed (hr) | Amount of Insulin Released (USP Insulin Unit) | |
|---|---|---|
| | Serum Alone | Serum + 300 mg % Glucose |
| 2 | 3.1 | 11.2 |
| 4 | 6.6 | 23.0 |
| 6 | 9.4 | 30.1 |
| 8 | 12.1 | 38.2 |
| 10 | 16.3 | 42.5 |
| 12 | 20.6 | 52.4 |
| 14 | 25.8 | 61.8 |
| 16 | 27.2 | 70.0 |
| 18 | 30.0 | 77.1 |
| 20 | 33.4 | 82.4 |
| 22 | 35.1 | 90.3 |
| 24 | 38.2 | 101.2 |

The results in Table 2 above show that during 24 hours, insulin was stably supplied from the supplier to the blood.

EXAMPLE 3

The insulin supplier used was of the type shown in FIG. 1 except that a glucose sensor was provided and interlocked with a motor for supplying the insulin solution. The tubular structure comprised 185 hollow fibers of cellulose acetate having an inside diameter of 180 μ and a wall thickness of 21μ, and the total length of that portion which contacted the blood was 3 cm. An aqueous solution (pH=3.0) of semi-lente insulin having a concentration of 60 mg% was passed through the hollow fibers. Both ends of the hollow fibers were bundled and held by a silicone resin (polydimethylsiloxane) and heparin was chemically bound to the surface of the silicone resin and the blood-contacting portion such as the external chamber using glutaraldehyde as a cross-linking agent. The capacity of the external chamber of the insulin supplier was 15 cc. From an inlet 8, human blood (containing 5% by weight of sodium citrate) 8 hours after collection was passed at a rate of 60 ml/min. The blood which left an outlet 9 was recycled to the inlet 8 through a tank. The oxidase electrode placed inside the external chamber was composed of three layers which comprised an inside layer comprising a platinum silver electrode wrapped with cellulose acetate, a central layer comprising a membrane of regenerated cellulose immobilized by glucose oxidase using glutaraldehyde and an outside layer comprising a polycarbonate membrane.

Table 3 summarizes the amount of insulin released to the blood when the insulin solution was passed at varying flow rates under the conditions described above. Insulin was traced in the same way as in Example 1 using a tracer which comprised mixing insulin labelled with $^{125}$I with non-labelled insulin, and measuring the γ-ray level in the blood.

Table 3 shows the amount (USP insluin unit) of insulin released into the blood for 10 minutes when the insulin solution was passed through each hollow fiber at a given flow rate.

TABLE 3

| Flow Rate of Insulin Solution (ml/min.) | Amount of Insulin Released per 10 Minutes (USP insulin unit) |
|---|---|
| 0.25 | 0.30 |
| 0.5 | 0.42 |
| 1.0 | 0.63 |
| 1.5 | 0.82 |
| 2.0 | 1.1 |
| 3.0 | 1.9 |

The results shown in Table 3 above demonstrate that the amount of insulin released into the blood increases as the flow rate of insulin through the tube increases and the total amount of insulin released can be controlled by varying the flow rate of insulin.

The same blood having glucose dissolved therein in a high concentration was added at 10 minute intervals to the circulating blood so that the glucose concentration in the blood became 100, 150, 200, 250, 300, 350 and 400 mg% respectively. In each instance, the potential difference detected by the glucose oxidase electrode and the total amount of insulin in the blood were measured while the sensor, amplifier and motor included in the insulin supplier of this invention were operative. Table 4 shows the potential differences detected by the glucose oxidase electrode at the varying glucose concentrations. The time required until the electrode detected the potential difference was not as short as desired, but the potential difference was closely correlated with the blood glucose concentration. Thus, the potential difference definity rose as the glucose level increased, and signals via the amplifier could affect the motor operation fairly definitely.

TABLE 4

| Blood Glucose Level (mg %) | Potential Difference Detected by Glucose Electrode (mV) | Amount of Insulin Released (mUSP insulin unit/min) |
|---|---|---|
| 100 | 0.08 | 24 |
| 150 | 0.16 | 31 |
| 200 | 0.24 | 74 |
| 250 | 0.37 | 111 |
| 300 | 0.54 | 119 |
| 350 | 0.56 | 121 |
| 400 | 0.83 | 152 |
| 450 | 0.90 | 160 |

The results shown in Table 4 above also show that with an increase in the concentration of glucose, the flow rate of the insulin solution increases, and depending on the amount of glucose, insulin is released into the blood in an amount required for metabolism in the human body.

Although there is some variations in the amount of insulin released until it became constant, insulin can be released in an amount sufficient to control the amount of glucose for metabolism (if enough response time is taken). Hence, such variations are not a problem. Accordingly, when the insulin supplier of this invention is used, insulin is released in an amount required for metabolism depending on the increase in the blood glucose level. While circulating through the body, insulin becomes a carrier for the movement of glucose through the cells. It is evident therefore that the insulin supplier of this invention can be used as a device for maintaining the blood sugar level always at a constant level.

EXAMPLE 4

This Example is an in vivo Example.

The example was performed using an insulin supplier of the type shown in FIG. 1. The tubular structure was the same as the type described in Example 1. Inlet 8 for blood was joined to the arterial radialis of a diabetic dog from which the pancreas had been removed and blood was introduced into the external chamber, and then the blood was discharged from outlet 9. Further, discharge of the blood was assisted by a shearing pump. Furthermore, the tube discharging the blood was joined to the splenic vein in order to circulate the blood back into the body of the diabetic dog. In this case, the average blood flow rate was 65 ml/min. An aqueous solution (pH=3.0) of regular insulin at a concentration of 50 mg% was introduced into the internal chamber. The insulin solution was circulated at flow rate of 20 ml/min. using a liquid conveying pump. The procedure was conducted for 24 hours. During this time, an aqueous solution containing 10 g of glucose was injected twice into the body of the dog (once after 8.5 hours and then after 14.5 hours). During the above time, 2 ml of the blood was removed from the dog's body every 2 hours as a sample, the concentration of the glucose in the blood was measured using a Glucose Analyzer. The results obtained are shown in Table 5 below.

TABLE 5

| Time Elapsed (hr) | Amount of Glucose in Blood (mg %) |
|---|---|
| 0 | 465 |
| 2 | 318 |
| 4 | 206 |
| 6 | 112 |
| 8 | 106 |
| 10 | 285 |
| 12 | 134 |
| 14 | 105 |
| 16 | 272 |
| 18 | 123 |
| 20 | 105 |
| 22 | 98 |
| 24 | 101 |

The results in Table 5 show that this supplier effectively provides medical treatment to the diabetic dog. Accordingly, the supplier not only supplements the secretion of insulin secreted by the pancreas but also the supplier provides a sufficient effect in response to the two introductions of the glucose.

While the invention has been described in detail and with reference to specific embodiments thereof, it will be apparent to one skilled in the art that various changes and modifications can be made therein without departing from the spirit and scope thereof.

What is claimed is:

1. A method for supplying insulin to a patient which comprises connecting the patient to an insulin supplier comprising a casing and at least one tubular structure, said tubular structure being formed of hollow fibers and constituting a polymeric semipermeable membrane comprising a polymer selected from a cellulose, polyvinyl alcohol or polyamide and having pores of 100 Å to 2μ in size to provide an internal chamber inside of the tubular polymeric semipermeable membrane and an external chamber outside of the tubular polymeric semipermeable membrane, either the internal chamber or the external chamber having at least one fluid-inlet and at least one fluid-outlet, said hollow fibers having a thickness of about 10 to 50μ and an inside diameter of about 50 to 400μ, introducing blood or another body fluid of said patient into that chamber which has said at least one fluid-inlet and at least one fluid-outlet and providing an aqueous solution or emulsion of insulin in the other chamber, whereby insulin in an amount required for metabolism within the body is supplied to the blood or the body fluid in response to the blood glucose level through the polymeric semipermeable membrane between the internal and external chambers continually over a period of time.

2. The process of claim 1 wherein the internal chamber is an insulin solution chamber.

3. The process of claim 1 wherein the insulin solution or emulsion is pressurized.

4. The method of claim 3 wherein the cross-sectional shape of the tubular structure is triangular, polygonal, circular or elliptical.

5. The process of claim 1 wherein blood of said patient is introduced into said chamber.

6. The process of claim 1 wherein both the internal chamber and the external chamber have at least one fluid-inlet and at least one fluid-outlet, and an aqueous solution or emulsion of insulin is passed through the other chamber by means of said at least one fluid-inlet and said at least one fluid-outlet being linked to means for flowing a fluid.

7. The process of claim 6 wherein the insulin is passed through the internal chamber.

8. The process of claim 6 which includes determining the glucose level in the blood or body fluid by means of a sensor placed into the chamber into which the blood or body fluid is introduced and linking said sensor to the means for flowing the insulin fluid, whereby the flow rate of the insulin fluid is varied in response to the glucose level determined.

9. The process of claim 6 wherein the blood or other body fluid is blood.

10. The method of claim 1 wherein the cellulose is cuprophane, cellulose acetate or regenerated cellulose.

* * * * *